(12) United States Patent
Hochman

(10) Patent No.: US 7,449,008 B2
(45) Date of Patent: Nov. 11, 2008

(54) DRUG INFUSION DEVICE WITH TISSUE IDENTIFICATION USING PRESSURE SENSING

(75) Inventor: Mark N. Hochman, Lake Success, NY (US)

(73) Assignee: Milestone Scientific, Inc., Livingston, NJ (US)

( * ) Notice: Subject to any disclaimer, the term of this patent is extended or adjusted under 35 U.S.C. 154(b) by 859 days.

(21) Appl. No.: 10/827,969

(22) Filed: Apr. 20, 2004

(65) Prior Publication Data
US 2005/0004514 A1    Jan. 6, 2005

Related U.S. Application Data

(60) Continuation-in-part of application No. 09/766,772, filed on Jan. 22, 2001, now Pat. No. 6,786,885, which is a division of application No. 09/201,464, filed on Nov. 30, 1998, now Pat. No. 6,200,289.

(60) Provisional application No. 60/502,379, filed on Sep. 12, 2003, provisional application No. 60/081,388, filed on Apr. 10, 1998.

(51) Int. Cl.
*A61M 31/00* (2006.01)
(52) U.S. Cl. ...................................................... 604/67
(58) Field of Classification Search .................. 604/66, 604/67, 65, 123, 151, 118, 183, 218, 232, 604/152, 500, 154, 155; 600/561, 562
See application file for complete search history.

(56) References Cited

U.S. PATENT DOCUMENTS

| | | | |
|---|---|---|---|
| 4,215,699 A | 8/1980 | Patel | |
| 5,295,967 A * | 3/1994 | Rondelet et al. | 604/154 |
| 5,425,716 A | 6/1995 | Kawasaki et al. | |
| 5,902,273 A | 5/1999 | Yang et al. | |
| 6,113,574 A | 9/2000 | Spinello | |
| 6,159,161 A | 12/2000 | Hodosh | |
| 6,171,276 B1 | 1/2001 | Lippe et al. | |
| 6,494,882 B1 * | 12/2002 | Lebouitz et al. | 606/45 |
| 2004/0215080 A1 | 10/2004 | Lechner | |

\* cited by examiner

*Primary Examiner*—Nicholas D Lucchesi
*Assistant Examiner*—Christopher D Koharski
(74) *Attorney, Agent, or Firm*—Notaro & Michalos P.C.

(57) ABSTRACT

An automatic injection device includes a drive mechanism and a sensor used to determine an internal characteristic such as a force or internal pressure generated during an injection process. This characteristic is then used as a control parameter by a microprocessor or controller to determine the exit pressure of the fluid expelled by the device. This exit pressure is then used to identify the kind of tissue in which the injection is being introduced.

17 Claims, 8 Drawing Sheets

DRUG INFUSION DEVICE WITH TISSUE IDENTIFICATION USING PRESSURE SENSING

RELATED APPLICATION

This application claims priority to U.S. Provisional application Ser. No. 60/502,379 filed Sep. 12, 2003 and incorporated herein by reference.

This application is also a continuation in part application to application Ser. No. 09/766,772 filed Jan. 22, 2001 now U.S. Pat. No. 6,786,885, which is a divisional of application Ser. No. 09/201,464 filed Nov. 30, 1998 now U.S. Pat. No. 6,200,289 claiming priority to provisional application Ser. No. 60/081,388 filed Apr. 10, 1998, all incorporated herein by reference.

BACKGROUND OF THE INVENTION a. Field of Invention

The present invention relates generally to improvements to the delivery of drugs, particularly to systems for subcutaneous injection/aspiration. More specifically this invention provides a method and device to the identification of specific tissue types (or soft-tissue density types) based on using a pressure measurement.

b. Description of the Prior Art

Infusion pumps devices and systems are well known in the medical arts, for use in delivery or dispensing a prescribed medication to a patient. The administration of prescribed drugs has been described in the literature as administration to a patient through infusion tubing and an associated catheter or the like, thereby introducing the drug intravenously. These systems are usual capable of determining infusion line occlusion. Line occlusions cause the pressure in the syringe to increase. Systems in the prior art have been developed to identify a predetermined threshold or to monitor pressure to determine means for selecting ranges of occlusion pressures to insure patient safety. U.S. Pat. Nos. 5,295,967; 4,731,058; and 5,080,653 show systems (with syringe pumps or the like) which are adequate for the intended use of intravenous drug delivery and more specifically for monitoring occlusion during infusion. However, these systems do not provide a means for drug delivery or aspiration subcutaneously via a hypodermic needle.

Accurately positioning a hollow-bore needle within tissues to delivery medication within tissue structures has long been a challenge in both medicine and dentistry. The inability to accurately position a hollow-bore needle within specific tissues (i.e. soft-tissues) or organs can lead to a failed medical objective. Locating pathologic tissue types (i.e. neoplasia, tumors, cysts and the like) is critical to aspiration of these tissues as well as the infusion of therapeutic medications to treat these local lesions of the body. Hence locating a specific anatomically site has been previously assisted with the use of ionizing radiation, ultrasound, MRI, electrical-stimulators and other invasive diagnostic devices that require secondary techniques to be employed to assist the practitioner to determining the accuracy of the placement of a needle within tissue.

Pain, tissue damage and post-op complications have long been tolerated as negative side effects from the use of existing hypodermic drug delivery injection systems. This is well documented in both the dental and medical literature. The pain and tissue damage are a direct result of uncontrolled flow rate in conjunction with excessive pressures created during the administration of drug solutions within the tissue spaces. Subjective pain response of a patient has been demonstrated to be minimized at specific flow rates during the administration of a drug. Also, it has been scientifically demonstrated that particular pressures (excessive without occlusion, per se) for a specific tissue type will cause damage. However, the present inventor has discovered that the amount of pain felt by a patient can be minimized with the use of a specific flow rate range in conjunction with a specified exit pressure range during the delivery of fluids (drugs). Moreover when drugs are delivered at this prescribed low ranges of pressure and fluid flow, tissue damage is minimized as well. It is also necessary that this system have the capability to aspirate under controlled conditions of rate and pressure to avoid the same negative side effects during fluid movement. U.S. Pat. No. 5,180,371 to Spinello, incorporated herein by reference, presented an invention, which allowed a rate to be set for the drug via a hypodermic needle. That invention however did not disclose means of determining, detecting or monitoring pressure during the administration of a drug. U.S. Pat. No. 6,113,574 to Spinello discloses an injection device in which a pressure sensor switch is used to determine during a PDL injection whether the liquid from a needle is injected into the proper location, or is leaking out into a patient's mouth or to some other location. However, the patent does not address the problem of identifying the tissue in which an injection is being made.

During the early 1980's, several researchers ( See for instance Rood, *The Pressure Created by Inferior Alveolar Injections*, British Dental J. 144:280-282 (1978); Walton and Abbot, *Periodontal Ligament Injection; a Clinical Evaluation* JADA. (October 1981); Smith and Walton, *Periodontal Ligament Injection; Distribution of Injected Solution* Oral Surg 55:232-238 (1983)) clearly demonstrated and concluded that the pressure created by the injected fluid is critical to preventing tissue damage and a pain response. Variability, different collagen types and connective tissue densities result in different tissue compliance and distensibility. These variations are found between subjects and within the individual subjects. Rood in his 1978 article states that "[t]he relationship between rate of injection and pressure rise seen clearly with the smaller volumes was lost when 2.0 ml was injected. Several high pressures were recorded and some unexpected low ones. Many tracings showed a pattern suggestive of tissue disruption and it is possible that said low pressures were due to the fluid no longer being contained within the pterygomandible space as the volume injected was similar to the previously estimated volume of the tissue space." Hence, it appears that the rate of flow is not directly related to pressure during an interstitial injection.

Smith and Walton described in their article identified supra discussed above that they have performed a histologic animal study (canines) using a technique to calibrate manual pressures produced. They concluded that the "Volume injected and needle location were not always related to distribution. Injecting under moderate to strong back pressure gave deeper and more widespread dye penetration." This once again confirms that pressure is the critical variable in the distribution of the solution within tissues and the volume is not always related to the pressure produced.

Pashley, Nelson & Pashley in "*Pressures Created by Dental Injections*" (J Dent Res 1981) used a pressure transducer and fixed flow rate created by a motor driven traditional syringe clearly demonstrated that different tissues have different tissue compliance. Interstitial pressure variability was statistically and clinically significant even with a fixed flow rate. Therefore, it may be concluded that they produced great variations of pressure by using a metered flow rate.

Pertot and Dejou described in their article "*Effects of the force developed during periodontal ligament injections in dogs*" (Oral Surg. Oral Med, Oral Pathol. 1992) how they used a syringe coupled to a miniature force transducer and found a positive correlation between the number of osteoclasts and the force applied on the syringe plunger, which indicated the pressure generated in the PDL space enhanced osteoclastic activity. This experiment again indicates that pressure is a critical factor to tissue damage and is dependent on the resistance encountered and not the flow rate of the solution into the tissues.

Prior art references are known which attempt to utilize a pressure transducer to measure the pressure within the syringe (See for instance U.S. Pat. No. 5,295,967). A major deficiency of these systems is their inability to adjust the flow rate and/or pressure of the fluid to compensate for changes in resistances throughout the system, or to the exit pressure. (Exit pressure refers to the fluid pressure just downstream of the needle tip within the patient's body). Moreover, the prior art references fail to provide any means of determining this exit pressure.

U.S. Pat. No. 6,200,218, a parent of the present application and incorporated herein by reference, discloses an automatic injection device that includes a drive mechanism that causes a therapeutic fluid to flow from a cartridge supported by a cartridge holder, a tube and a handle with an injection needle. The drive mechanism is connected to an electric motor and a sensor positioned at the motor output that measures the force applied by the motor to the drive mechanism. This force is then used to determine an internal characteristic such as a force or internal pressure generated during the injection process. This characteristic is then used as a control parameter by a microprocessor or controller which generates corresponding commands to the drive mechanism. In a particularly advantageous embodiment, the characteristic is used to calculate an exit pressure at which fluid ejected by the device through an elongated tube. The electric motor, is then operated in such a manner that the exit pressure is maintained at a predetermined level to insure that a patient does not suffer pain and/or tissue damage.

SUMMARY OF THE INVENTION

The present invention provides a method and device that enables the practitioner to utilize a diagnostic and therapeutic device simultaneously. The current device utilizes the inherent tissue density or resistance of fluid pressure within that tissue to identify the accuracy of placement of a needle within specific tissues. Each tissue has its own pressure density characteristics which are represented as measurable pressures that can be elicited within a given tissue type. The density or resistance of the tissue is measured using the pressure/force of a fluid infused from a computer-controlled drug delivery system capable of detecting pressure resistance during infusion. The pressure resistance measure is converted into a visual as well as audible signal on a continuous basis. The measurements are then presented to the doctor so that the doctor can determine or confirm whether the injection is being delivered to the right tissues. In addition, the measurements are also recorded for later review and documentation of the clinical event. Upper limits of pressure as well as control of flow-rate can be pre-defined to ensure that excessive pressure and/or flow-rate are not used during this process.

The present application also provides alternate means of determining force or pressure within an automatic injection device. In one embodiment, the electrical energy or power used by the motor is used as a parameter indicative of the force. In another embodiment, a change in a dimension of various elements of the fluid delivery system are used as parameters. This dimensional change is then converted into signal indicative of the internal force/pressure. For example, some of the elements that exhibit dimensional changes responsive to increased internal forces or pressures include the cartridge or reservoir holder, including its wings, the tube used to deliver the drug from the cartridge to the handpiece, the needle hub and/or its elements. The sensor for determining this dimensional variation may be for example an optical sensor.

A third method is to determine the stress or strain on the motor housing and/or the supporting members of the drive. A standard electronic strain gauge may be used for making this measurement.

Briefly, a system in accordance with this invention for dispensing a fluid by injecting the same into a patient includes a mechanical assembly and an electrical controller. The mechanical assembly consists of a drive mechanism and a disposable portion consisting of a fluid storage device such as a syringe, a carpule and the like, and a fluid delivery section including a tube coupled to said fluid storage device and terminating in a needle adapted to be inserted into the subject tissue. The drive mechanism includes a housing with an internal motor and a mount for mounting the fluid storage device on the housing. The fluid storage device includes a reciprocating plunger. A coupling is used to move the plunger with said motor. If a carpule is used for the fluid storage device, an adapter is also provided to allow the same mount to secure the carpule as well. The mount is arranged and constructed to secure syringes or carpules having a large variety of sizes.

A transducer is used to sense the force or pressure generated by the motor and applied by the plunger within the fluid storage device. In one aspect of the invention, the transducer measures the force between the carpule adapter and the remaining housing of the device. In another aspect of the invention, the transducer includes a size sensing device that senses a change in dimension of an element of the device, said change being indicative of the force or pressure of the drug within the system and the exit pressure. For example, the change in size of the tubing may be used as an indicia of this force or pressure. In another embodiment, the pressure within the tube is measured externally and used as a means of determining the exit pressure.

The motor, the coupling associated with the motor and the electronic controller discussed below is at least partially disposed within the housing for protection.

The fluid storage device is filled and a setup process is initiated during which various operational parameters are calculated, retrieved or received from the clinician. The clinician also specifies the fluid flow rates and peak exit pressure and a total amount of fluid to be dispensed. Then he operates a pneumatic control such as a foot pedal and initiates the fluid flow. Alternatively, commands may be initiated by the clinician either electronically or by voice commands. During dispensing, the output from the transducer is used to calculate the current exit fluid pressure. If this exit pressure approaches a certain threshold, the fluid flow rate is automatically reduced to prevent excessive exit pressure, thereby ensuring that the patient does not suffer undue pain and no tissue is damaged. Several optional features are also provided including aspiration, purging or charging the media with or without air.

Alternatively, the system may be operated in a biopsy mode in which the entry pressure and the outbound or withdrawn fluid flow rate are the relevant control parameters.

Throughout the process, the clinician is provided with constant current information on the ongoing process, both visual and aurally, including the current flow rate, total volume ejected or aspired, exit or entry pressures and other parameters. The slave microprocessor receives commands from the master microprocessor and generates the drive signals required to operate the motor.

DETAILED DESCRIPTION OF THE INVENTION

The subject invention pertains to a system for delivering drugs such as an anesthetic, under pressure into a patient's tissues. Importantly, due to a variety of factors, injected fluid disperses through a tissue at different rates, causing the fluid exit pressure to vary. The present inventor has discovered that this exit pressure (or an internal pressure related to the exit pressure) is indicative of, and may be used to identify several types of tissues.

Figure 1:
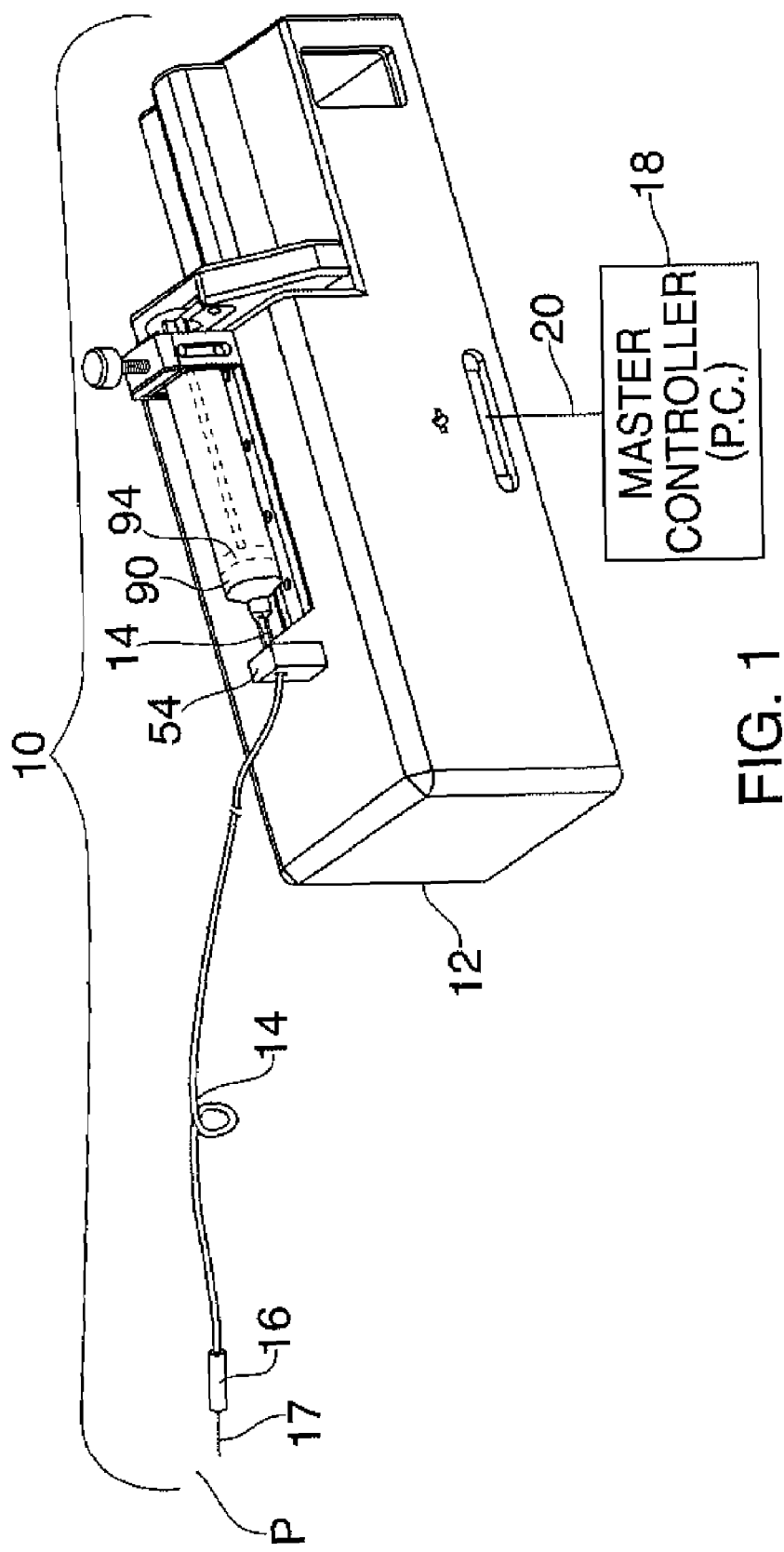
FIG. 1 shows a diagram illustrating the major components of the infusion device constructed in accordance with this invention.
Figure 2:
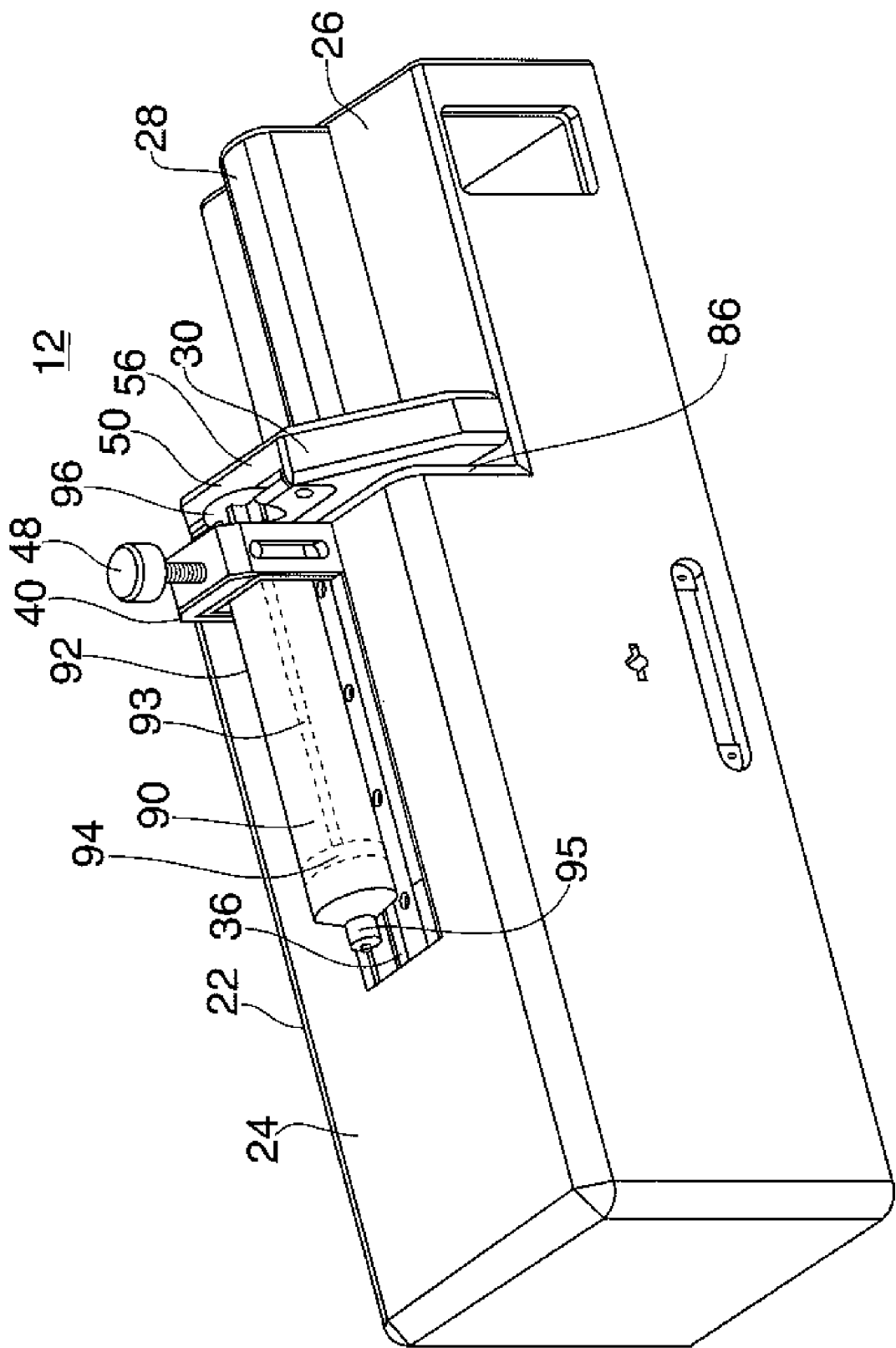
FIG. 2 shows an orthogonal view of the drive mechanism of FIG. 1.
Figure 3:
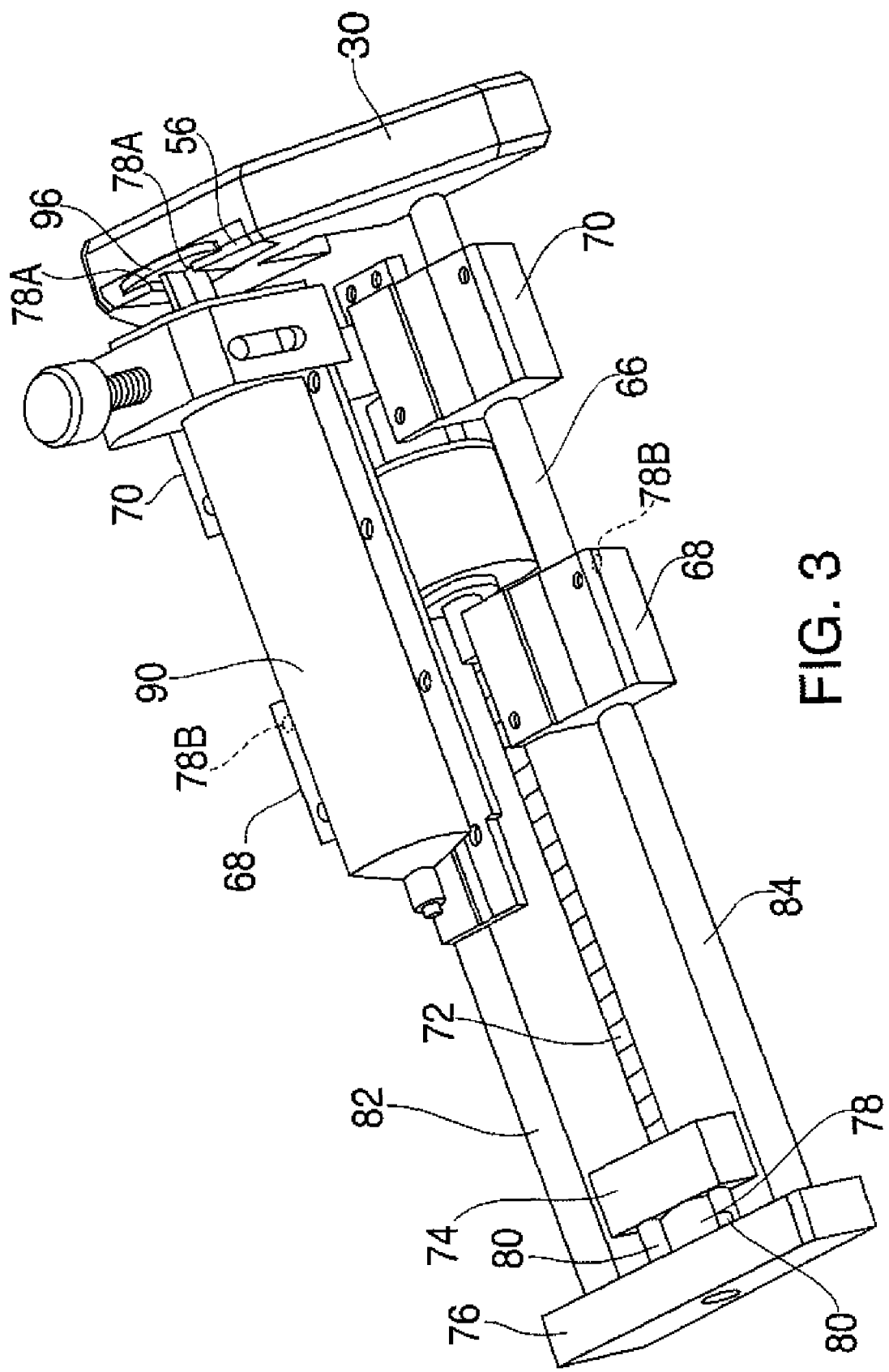
FIG. 3 shows internal details of the drive mechanism of FIG. 1.

The mechanical assembly for the subject system is illustrated in FIGS. 1 and 2 and the electronic controller 150 for the system is shown in FIG. 3.

A drug delivery system 10 constructed in accordance with this invention includes drive mechanism 12, a delivery tube 14 and a handle 16 terminating with a needle 17. More particularly, a syringe 90 (or other fluid storage device or container) is mounted on the drive mechanism with one end of tube 14 being coupled to the syringe 90. The tube 14, handle 16 and needle 17 in the embodiments of FIGS. 1 to 3, form injection means of the invention for administering the drug fluid at a dynamic exit fluid pressure to a patient tissue type for receiving the drug fluid. The drive mechanism 12 operates a plunger 94 to selectively eject fluid out of the syringe 90, through the tube 14, handle 16, and needle 17 or alternatively to draw fluid in. The drive mechanism 12, plunger 94 and syringe 90 form a pumping mechanism for the device. The drive mechanism 12 is associated with an external controller for selecting various operational parameters discussed in more detail below. This external controller may be provided on the housing of the drive mechanism or may be provided as a separate control unit 18 coupled to the drive mechanism 12 by a cable 20. The control unit 18 may be for instance a PC or laptop computer. Alternatively, the control unit 18 may be internal.

Details of the drive mechanism 12 are seen in FIG. 2. The drive mechanism 12 includes a housing 22 with a top surface 24 and intermediate surface 26 disposed below top surface 24. On surface 26 there is formed a rail 28 extending along the longitudinal axis of housing 22. A platform 30 which is disposed on the rail 28 can be reciprocated back and forth in parallel with said longitudinal axis, as described in more detail below.

On top surface 24 there is a clamp 40. The clamp 40 has a generally C-shaped body. A screw with a head 48 extends through a threaded hole (not shown) in the body of the clamp 40. Platform 30 has a slot 56.

Inside the housing 22, there is provided a motor 66 (FIG. 3). Threaded through the motor 66 there is a worm screw 72. The worm screw 72 is arranged so that as the motor 66 is activated, the worm screw 72 moves in one direction or another, dependent on its direction of rotation, in parallel with the longitudinal aids of the housing 22. One end of the worm screw 72 is non-rotatably attached to a pad 74, coupled to a platform 76. Two short rods 80 are used to couple the pads 74 to platform 76, to prevent the transmission of rotational forces generated by the motor 66 to the platform 76.

Two columns or rods 82, 84 extend between platforms 30 and 76 and secure these two members together. These rods 82, 84 are slidably supported by two pairs of bushings 68, 70 on the housing 22. Except for these bushings, the platforms 76 and 30 are floating respectively inside and outside the housing 22. Rods 82, 84 extend through wall 86 extending between surfaces 24 and 26 via holes (not shown). The rail 28 is hollow and aligned with the worm screw 72 to allow the worm screw 72 to move longitudinally along its axis through the housing 22.

Typically, the syringe 90 has a barrel 92 on surface 24. The barrel 92 has a finger tab resting in a slot formed on the face 24. The finger tab and the slot have been omitted from the drawings for the sake of clarity. The syringe 90 also includes a plunger 94 reciprocated within the barrel 92 by a shaft 93. The shaft terminates in a finger pad 96 resting in slot 56 of platform 30. The syringe 90 is secured to the housing 22 by clamp 40 and screw 48. The syringe terminates with a Luer lock 95 used to connect the syringe to tube 14.

When the motor 66 is activated, as discussed below, it forces the worm screw 72 to move in one direction or another. The worm screw in turn forces the platforms 30, 76 and rods 82 and 84 to move in concert as well, thereby forcing the plunger 94 to reciprocate within the barrel 92. The only elements which move in and out of the housing are the rods 82, 84. Hence most of the critical elements of the system are protected within the housing from tampering, or spilled fluids. Moreover, the drive mechanism 12 is adapted to receive and operate with syringes of various diameters and lengths. Similarly, the delivery tube 14, handle 16 and needle 17 may have any size desired. More details of the syringe and the motor drive, the worm screw and its coupling to the platform 30, are described in U.S. Pat. No. 6,200,289. Moreover, this patent further describes a load cell 78 disposed between platform 76 and pad 74 and arranged to transmit and measure the force between the pad 74 and platform 76. This load cell 78 is bidirectional so that it can measure both stress and strain dependent on whether the worm screw 72 is moving to the left or to the right as determined in FIG. 3. In the present invention other means are disclosed that replace this load cell.

In one embodiment, the apparatus includes a pair of pressure sensors 78A are disposed between finger pad 96 and the walls of slot 56. The sensors 78A are arranged to measure the force applied between the platform 30 and the finger pad 96.

In another embodiment, sensors 78B are provided between the bushings 68 and the sidewalls of the housing 22. In this manner, the sensors 78B can measure the force (or strain) resultant from the force applied by the motor on the syringe plunger 94. Alternatively, a similar load cell may be placed between the syringe tab and the housing 22. The sensors may be load cells, for instance a Model S400 load cell made by the SMD, Inc. of Meridien, Conn.

In yet another embodiment, shown in FIG. 1, the tubing 14 passes through a hole in a size gauge 54. When the tubing 14 is pressurized, it expands, and therefore, the size of the tubing is indicative of the pressure applied thereto by the plunger. The size gauge 54 monitors the size (e.g. cross-sectional dimension, or diameter) of the tubing 14 and provides this parameter to the master controller 18. For example, gauge 54 may include one or more LEDs and an array of light sensors with tubing disposed therebetween. The size of the tubing is determined by the number and/or position of the light sensors occluded by the tubing.

Figure 8:
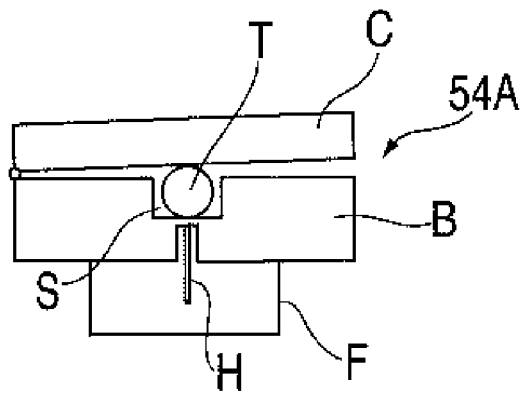
FIG. 8 shows an alternate embodiment of a pressure gauge using the size of the tubing.

FIG. 8 shows a cross-section of another gauge 54A that may be used instead of gauge 54. It consists of a base B with a slot S holding the tubing T. A hinged cover C holds the tubing T in place. A force sensor FS available off the shelf is inserted through a hole H and rests against the tubing T. As the tubing expands and contracts due to pressure changes, it applies a force on the force sensor. Experimental data shows that this gauge 54A has a fairly linear output and easy to calibrate for various pressures.

Figure 9:
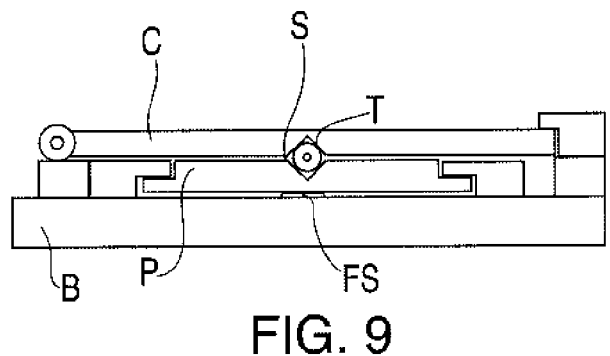
FIG. 9 shows another embodiment of the pressure gauge using the size of the tubing.

FIG. 9 shows another gauge 54B that can be used instead of gauge 54. This gauge is similar to the one in FIG. 8 with the exception that a groove is made in the cover C and the tube is resting on a floating platform P disposed above the force sensor. The force generated by the pressure within the tube is transmitted by the floating platform P to the force sensor FS. Again, the response of this gauge is linear and easy to calibrate.

Figure 3A:
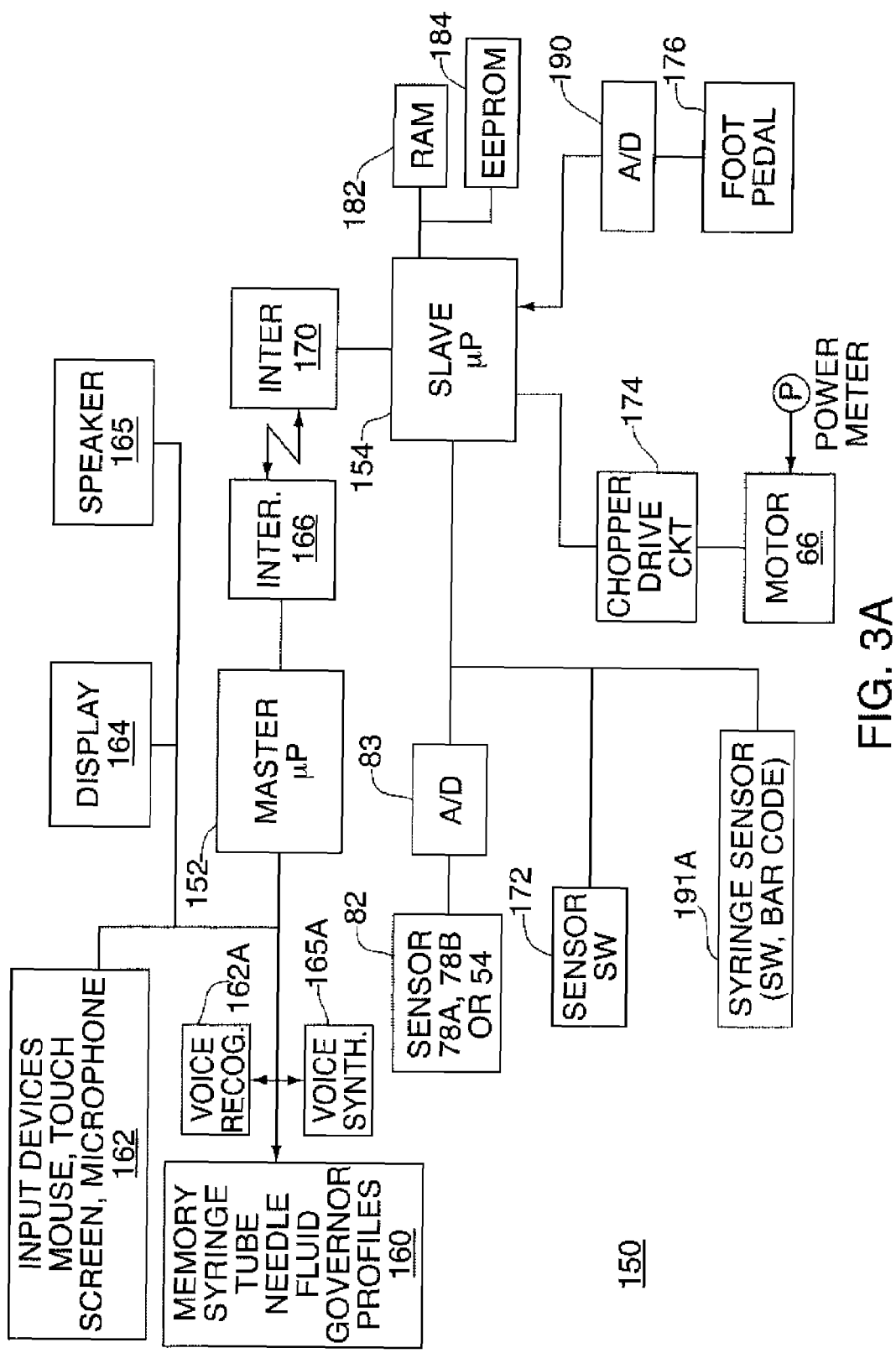
FIG. 3A shows a block diagram of the electronic controller of FIG. 1.

FIG. 3A shows a block diagram of the electronic controller 150. The controller 150 includes two microprocessors: a master microprocessor 152 and a slave microprocessor 154. Slave microprocessor 154 is used to derive the signals that actually drive the motor 66 and to collect information regarding the position of the platforms 30, 76.

The master microprocessor 152 is used to collect information regarding the rest of the system, including the syringe 90, and its contents, the tube 14, the handle 16 and so on, and to generate control signals for the slave microprocessor 154 necessary for operating the motor 66 to deliver the contents of the syringe 90.

Physically, the slave microprocessor 154 and its associated circuitry are disposed within the housing 22. The master microprocessor 152 is incorporated into control unit 18 which is coupled to the housing 22 through cable 20 as shown in FIG. 1. The microprocessor 152 is associated with a memory 160, input devices 162, display devices 164 and an interface 164.

Memory 160 is used to store programming and data for the master microprocessor 152. More specifically, the memory 160 is used to store six or more data banks, each of said data banks being dedicated to the following information: (a) syringes; (b) tubing; c) needles; (d) fluids; (e) governor parameters; and (f) profiles consisting of a plurality of parameters for a particular procedure to be performed. Each of these parameters is used to determine the control signals generated for the slave microprocessor 154. Each of these data banks contains the appropriate parameters for various commercially available products, or alternatively, parameter data derived using a specific algorithm. Information regarding the various elements for a particular configuration is entered through input devices 102 and is confirmed on the display device 164. These input devices may include a keyboard, a touch screen, a mouse, as well as a microphone. If a microphone is included, voice commands are interpreted by a voice recognition circuit 162A.

The display device 164 is further used to provide an indication as well as instructions on the operation of the system 10. The commands for the operation of motor 66 are generated by master microprocessor 152 and transmitted to an interface 162. Microprocessor 152 is further provided with a speaker 165 used to provide various oral messages, including spoken pre-recorded or synthesized words, (generated by a voice synthesized circuit 165A) chimes, and so on, to provide instructions to the clinician and to provide other information about the current status of the whole system and its elements without the need for the clinician to look at the displays all the time.

The slave microprocessor 154 receives these commands through cable 20 or other connection means and interface 170.

Also associated with the slave microprocessor 154 are one or more position sensors 172 and a chopper drive circuit 174. As previously mentioned, the force or pressure generated within the system is measured by sensors 78A, 78B, 54, 54A, 54B.

Also associated with slave microprocessor 154 is a foot switch or pedal 176. Preferably foot pedal 176 consists of an air chamber with a flexible side wall, said side wall being arranged to change the volume of air and pressure within said chamber in response to activation by a human operator. A pressure sensor (not shown) is part of the foot pedal and is arranged to provide information about said pressure to slave microprocessor 154 via a corresponding A/D converter 190. Foot pedals of this kind are well known in the art and therefore its details have been omitted.

The sequence of operation for the system 10 are similar to the ones described in U.S. Pat. No. 6,200,289 and are not repeated here. Moreover, the algorithm disclosed in said patent is also applicable for converting the parameter obtained from the sensors 78A, 78B or 54 into a corresponding exit pressure.

In another embodiment, the power required to drive motor 66 is monitored. For example, the master controller 150 maybe provided with a power meter P that monitors this power, for example, by measuring the voltage and current applied thereto. This power is, of course, indicative of the force applied by the motor and is used in the same manner as the output of the sensors 78A, 78B or 54.

The system has been described so far as performing an injection process. However, it is obvious to one skilled in the art that it can be used just as effectively to perform a biopsy, for instance to perform a spinal tap, or other similar anaerobic procedures. Essentially the same parameters can be used for this process, with some minor modifications. For instance, instead of defining an exit pressure, the clinician now defines an entry pressure.

Figures 4, 7:
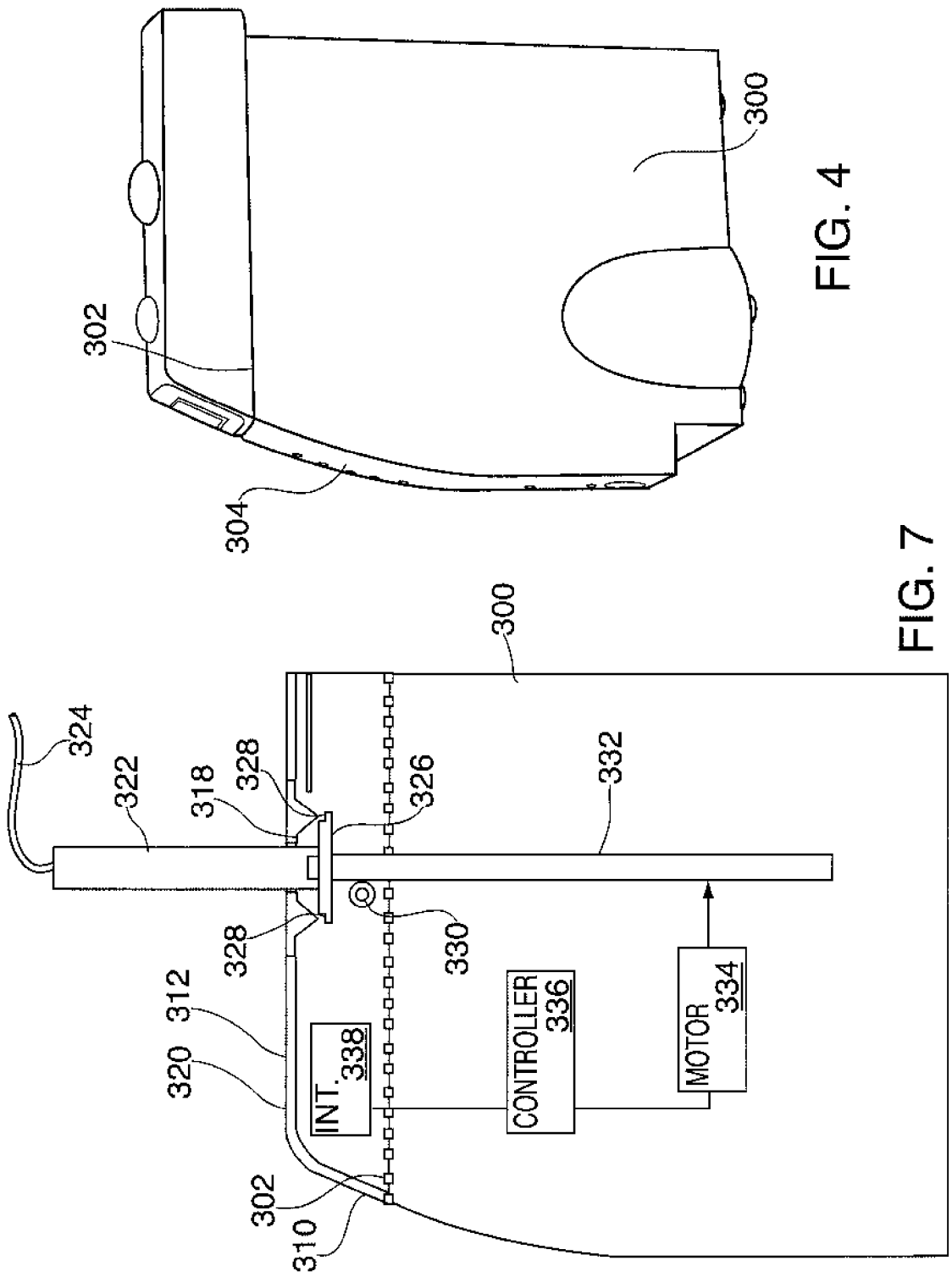
FIG. 4 shows a side view of the housing of a different type of infusion device with an adapter for pressure sensing.
FIG. 7 shows a somewhat diagrammatic cross-sectional view of the housing of FIG. 4.
Figure 5:
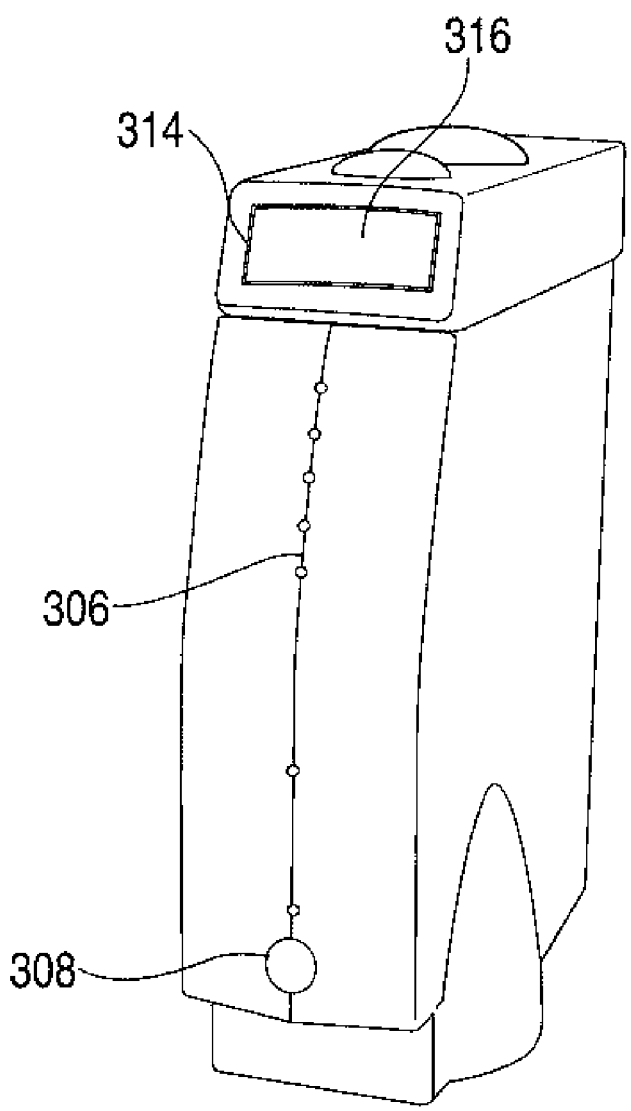
FIG. 5 shows an end view of the housing of FIG. 4.
Figure 6:
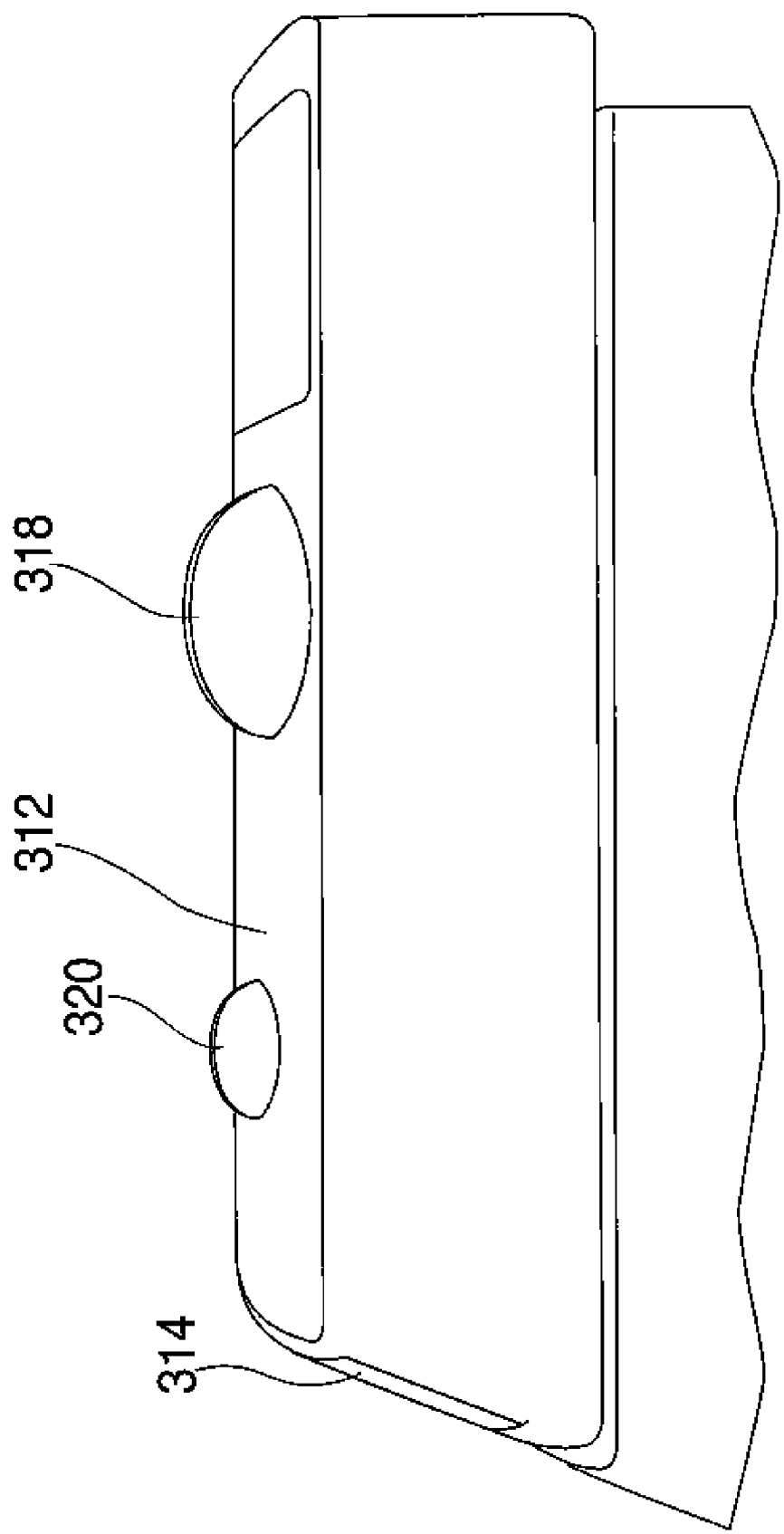
FIG. 6 shows an enlarged view of the adapter of FIG. 4.

In the embodiment discussed so far, it is assumed that a fluid is dispensed from the syringe 90 and, therefore, this syringe 90 must be preloaded with said fluid either by the manufacturer, or must be filled at the site by the clinician or an assistant prior to the start of any operation. In many procedures, however it is more desirable to provide the fluid to be dispensed in a cartridge. Commonly owned U.S. Pat. No. 6,152,734 an injection device is described that includes a housing with a motor driven shaft. On top of the housing, a receptacle is provided for accepting a cartridge holder. The cartridge holder receives a cartridge with an anesthetic. The holder has a top wall connected to the proximal end of a tubing. The distal end of the tubing is used to deliver an anesthetic through its distal end. In accordance with this invention, a sensor module is added on top of the housing. Referring first to FIGS. 4, 5 and 6, the housing 300 has a top surface 302 and a front surface 304. Disposed on the front surface 304 there are a plurality of indication lights and one or more control buttons 308. According to this invention, a sensor module 310 is mounted on top surface 302. This module 310 includes its own upper surface 312 and front surface 314. On front surface 314 there is an LCD display 316.

On the top surface 312 there is provided a receptacle 318 and a hole 320 having the same shape and size as the corresponding elements on the top of the housing 300 described and illustrated in U.S. Pat. No. 6,152,734. Referring now to FIG. 7, attached to module 310 there is a cartridge 322 connected to the proximal end of a tubing 324. The distal end of the tubing 324 is connected to a needle, a catheter or other similar injection means that are similar to the tube 14, handle 16 and needle 17 of the embodiments of FIGS. 1 to 3, for administering the drug fluid at a dynamic exit fluid pressure to a patient tissue type for receiving the drug fluid. When not in use, this injection means can be stored in hole 320. The bottom 326 of the cartridge holder 322 is shaped so that it can be inserted quickly and easily into the receptacle 318 and form an interference fit therewith. As described in U.S. Pat. No. 6,152,734, preferably a quick-connect coupling is provided between the bottom 328 and the receptacle 318 so that the cartridge holder 322 can be quickly and easily installed onto and removed from the receptacle. The cartridge holder 322 holds a cartridge with an anesthetic or other medicinal substance (not shown).

Importantly, according to this invention, one or more sensors 328 are positioned between the bottom 326 of cartridge holder and the walls of receptacle 318. These sensors may be pressure sensors or other similar sensors used to monitor the force applied to the liquid being ejected through tubing 324.

As discussed above, disposed in housing 300 there is a plunger 332, which, with the cartridge 322 and a motor 334, form the pumping mechanism for this embodiment of the invention. Module 312 holds optionally a plunger sensor 330 that is disposed in close proximity to, or in contact with the plunger 332. As the plunger moves upward, its tip enters into the cartridge in the cartridge holder 322 and forces its contents to be ejected through tubing 324. Moving plunger 332 downwardly causes aspiration. The plunger sensor 330 measures the direction and, optionally, the rate of movement of the plunger 332.

This plunger 332 is reciprocated vertically by a motor 334. The motor 334 is controlled by a controller 336. The sensors 328 and 330 are coupled to an interface 338. This interface transmits the information from the sensors 348, 330 to the controller 336. The controller then operates the motor to cause the plunger 332 in the same manner, and using the same algorithm as the plunger 94 in FIGS. 1-4. The information associated with this operation, and any other information are displayed on the display 316.

In this arrangement the sensors may also be used to detect basic operations of the unit such as purging or auto-retraction of this plunger. As the cartridge holder is inserted within the socket of the drive unit the pressure sensors detect their placement and will then automatically purge air from the tubing line readying the system for use. When the cartridge holder is removed from the unit the pressure sensor can detect the removal and allow for automatic retraction of the plunger to the "home" position. Hence, the pressure sensors play a multipurpose role of detecting exit pressure as well as basic operations of the drive unit.

Importantly, the pressure may also be used as criteria to determine the tissue in which fluid is being injected by the device. Previous authors have investigated the clinical implications of interstitial pressure during dental injections. The present inventor has conducted research that demonstrates that using the device described herein, subcutaneous interstitial pressures could be accurately measured and recorded in real-time. It was also determined that a given range of pressures obtained with the device could be readily identified and associated with for specific tissue types. Interstitial pressures generated were correlated to the tissue densities type for particular anatomic locations.

Highly organized densely packed collagen fibers such as those found in certain oral tissues as in the periodontal ligament and gingival hard palate reduced the ability for diffusion of injected fluid, i.e. fluids are contained within a smaller area. This reduced ability for denser tissues to allow rapid redistribution of the drug results in higher internal pressure during injections. In contrast, loosely organized tissues with a connective stroma composed of a collagen matrix interposed with interstitial fluid and adipose tissues as those found in the mucobuccal fold and infratemperal fossa, result in lower interstitial pressure, as a result of the drug being spread through a larger tissue area.

Figure 10:
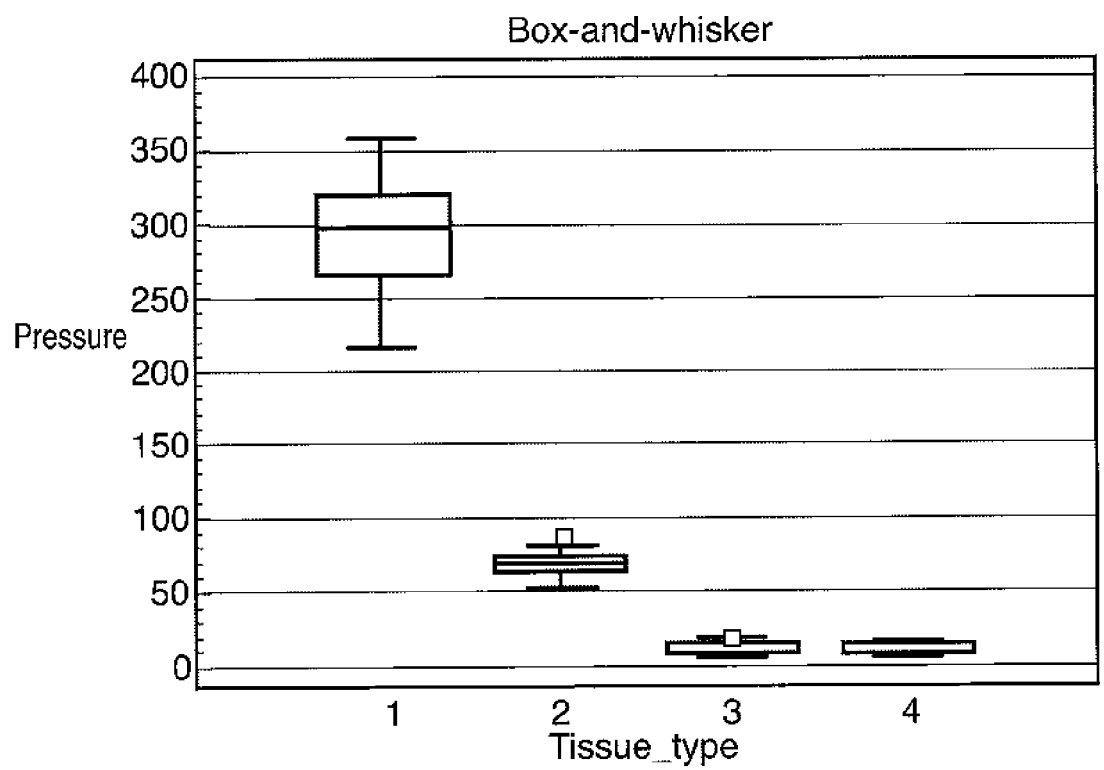
FIG. 10 shows a graph of typical pressure ranges for injections into four different types of tissues.

From this observation, a conjecture was made that there was a correlation between tissue density type and the injection process. More specifically, tests were conducted on the following types of injections:

Group 1—intraligamentary injections (PDL) (a.k.a. periodontal ligament injection), Group 2—the anterior middle superior alveolar palatal injection s(PI), Group 3—the supraperiosteal buccal infiltration (SBI) and Group 4—the inferior alveolar nerve block (IANB). FIG. 10 shows the various pressures obtained during these injections, and clearly illustrates the concept of using pressure (preferably exit pressure) as a means of identifying tissues.

In general, tissues may be categorized into the following types:

Type 1—Low density tissues, comprised of a loosely organized connective tissue matrix interposed with adipose tissue, intercellular fluids and small volumes of organized collagen fibers present. Examples of this tissue type are subcutaneous connective tissues of the maxillary buccal mucosa and infratermporal fossa. Examples of injections performed in these tissue types include; buccal infiltration and inferior alveolar nerve block.

Type 2—Moderate density tissues, comprised of a combination of densely packed collagen fiber bundles interposed with a small amount of glandular tissues and/or adipose tissue. A relatively small amount of intercellular fluids are found in these tissues. Moderate density tissues would also be represented by muscular tissue of the oral cavity. A moderate degree of collagen organization is found in these types of tissues. The tissue types are represented by the attached palatal gingiva, attached gingival tissues or muscle tissues of the oral cavity. Examples of injections performed in these tissue types include; palatal injections or injections into the attached gingiva.

Type 3—High density tissue composed of predominately dense highly organized collagen fiber matrixes. Examples of these types of tissues are the periodontal ligament and the muscle tendon attachments, an example of an injection performed in this tissue type is the PDL injection.

Moreover, the use of these techniques can be expanded to identify both mineralized and non-mineralized tissues, and even fluids as follows:

Non-mineralized tissues:
  Soft tissues, connective tissues, dermis (skin),
  Ligaments
  Adipose tissues (fat)
  Muscle
  Tendons
  Brain tissues
  Vessels Mineralized tissues:
  Cortical Bone
  Medullary bone
  Cartilage
  Teeth Neoplasms:
  Hard and soft lesions Fluid filled lesions
  Hematomas
  Cysts Fluids: Extacellular and Intra-cellular Fluids
  Intra-capsular fluids of Joints
  Intra-cranial fluids
  Cerebral Spinal fluids
  Lymph fluid As described above, the injection device continuously monitors a pressure, and preferably the exit pressure of the fluid during injection. Based on tables stored in its memory, the device is able to determine the type of tissues in which the injection is being injected. This information is displayed to the doctor (or other clinician). The doctor can then confirm that he is performing the injection in the desired tissues. In addition, for each type of tissue, preselected maximum allowable pressure limits and/or flow rates are stored that define either the maximum recommended pressures that patients usually tolerate, or other criteria. The parameters are stored in memory 160. As the pressure approaches this limit, a visual and/or audible alarm is generated for the clinician. In addition, data descriptive of the whole injection process is stored for future analysis, as discussed above.

The techniques described herein are equally applicable to human and animal tissues.

While the invention has been described with reference to several particular embodiments, it is to be understood that these embodiments are merely illustrative of the principles of the invention. Accordingly, the embodiments described in particular should be considered as exemplary, not limiting, with respect to the following claims.

The invention claimed is:

1. An apparatus comprising:
a housing;
a pumping mechanism in said housing;
a fluid container coupled to said housing and activated by said pumping mechanism to pump a drug fluid, said drug fluid exiting at a dynamic exit fluid pressure, said fluid container including injection means for administering the drug fluid at an exit fluid pressure to a patient tissue type for receiving the drug fluid;
a sensor arranged for determining said exit fluid pressure based on a measured parameter of at least one of said pumping mechanism and said fluid container; and
a controller for receiving said dynamic exit fluid pressure and having at least one memory data bank and at least one microprocessor, said memory data bank storing a plurality of known interstitial fluid pressures corresponding to different patient tissue types, the memory data bank also storing the measured parameter, said microprocessor generating an output based on the measured parameter and the patient tissue type for receiving said drug fluid and for correlating said exit fluid pressure to one of said known interstitial fluid pressures.

2. The apparatus of claim 1 further comprising: a pressure sensor for sensing a pressure within said pumping mechanism and a calculator for receiving said pressure within said pumping mechanism, and for deriving said exit fluid pressure.

3. The apparatus of claim 1 further comprising: said memory data bank containing information correlating exit fluid pressures to tissue types, wherein said controller receives said exit fluid pressure, compares said exit fluid pressure to said information and generates said output in accordance with said information, the tissue types being selected from the group consisting of: low density loosely organized connective tissue matrix interposed with adipose tissue, intercellular fluids and organized collagen fibers; medium density packed collagen fiber bundles interposed with glandular tissues and/or adipose tissue; muscular tissue; high density tissue composed of predominately dense highly organized collagen fiber matrixes; and mineralized tissue.

4. An apparatus comprising:
a pumping mechanism;
a fluid container coupled to said pumping mechanism to pump a drug fluid, said fluid exiting at a dynamic exit fluid pressure into a selected biological tissue type;
a sensor arranged to enable sensing and identification of specific biological tissue types based on the exit fluid pressures; and
a controller for receiving said dynamic exit fluid pressure and having at least one memory data bank and at least one microprocessor, said memory data bank storing a plurality of known interstitial fluid pressures corresponding to different biological tissue types, the memory data bank also storing measured parameters of at least one of said pumping mechanism and said fluid container, said microprocessor generating an output based on the measured parameter and the biological tissue type and for correlating said exit fluid pressure to one of said known interstitial fluid pressures.

5. The apparatus of claim 4; wherein said pumping mechanism includes: a container holding said drug fluid, a plunger reciprocating within said container and a motor responsive to signals from said controller and driving said plunger.

6. The apparatus of claim 5; wherein said sensor is disposed between said motor and said plunger to sense a force applied to said plunger.

7. The apparatus of claim 5; wherein said pumping mechanism includes: a flexible tubing leading said drug fluid to the biological tissue, and wherein said sensor is coupled to said flexible tubing.

8. The apparatus of claim 7; wherein said sensor includes: a size sensor sensing a dimension of said tubing.

9. The apparatus of claim 8; wherein said sensor includes: a light source and a light sensor, said light sensor generating an output indicative of an internal pressure within the tubing.

10. The apparatus of claim 7; wherein said tubing expands and contracts radially in response to the exit fluid pressure; and wherein said sensor includes: a tubing holder holding at least a portion of said tubing in a preselected position and a force sensor activated by said portion within said holder.

11. The apparatus of claim 10; wherein said holder includes: a base with a slot holding the tubing portion, a cover folded over said base and holding said tubing in said trough.

12. The apparatus of claim 11; wherein said holder includes: a base, a floating plate resting on said base, and a cover holding said tubing portion with said floating plate.

13. The apparatus of claim 12 further comprising:
a force sensor for sensing a force between the floating plate and said base.

14. The apparatus of claim 11 further comprising: a hole passing to said slot with said force sensor being disposed in said hole.

15. The apparatus of claim 4 further comprising: a power source providing power to said pumping mechanism, wherein said sensor determines the power provided to the pumping mechanism to determine said exit fluid pressure.

16. The apparatus of claim 4 further comprising: a housing and said pumping mechanism includes a cartridge holding said fluid.

17. The apparatus of claim 16; wherein said sensor includes: a load sensor disposed between said housing and said cartridge holder.

* * * * *